United States Patent
Mangiacotti

(10) Patent No.: US 10,501,719 B2
(45) Date of Patent: Dec. 10, 2019

(54) METHODS AND APPARATUS TO IMPLEMENT FLEXIBLE BIOREACTOR CONTROL SYSTEMS

(71) Applicant: GE HEALTHCARE BIO-SCIENCES CORP., Marlborough, MA (US)

(72) Inventor: Scott A. Mangiacotti, Marlborough, MA (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 282 days.

(21) Appl. No.: 14/424,699

(22) PCT Filed: Sep. 16, 2013

(86) PCT No.: PCT/US2013/059877
§ 371 (c)(1),
(2) Date: Feb. 27, 2015

(87) PCT Pub. No.: WO2014/043602
PCT Pub. Date: Mar. 20, 2014

(65) Prior Publication Data
US 2015/0218504 A1    Aug. 6, 2015

Related U.S. Application Data

(60) Provisional application No. 61/701,207, filed on Sep. 14, 2012.

(51) Int. Cl.
*G06F 8/36* (2018.01)
*C12M 1/36* (2006.01)
(Continued)

(52) U.S. Cl.
CPC .............. *C12M 41/48* (2013.01); *C12M 1/36* (2013.01); *G05B 19/0426* (2013.01); *G06F 8/36* (2013.01); *G05B 2219/32097* (2013.01)

(58) Field of Classification Search
None
See application file for complete search history.

(56) References Cited

U.S. PATENT DOCUMENTS 6,725,288 B2    4/2004  Yoshiyuki et al.
7,510,864 B2    3/2009  Krichevsky et al.
(Continued)

FOREIGN PATENT DOCUMENTS

CN    101241354 A    8/2008
GB    2399193 A    9/2004
(Continued)

OTHER PUBLICATIONS

CN Translation of First Office Action dated Oct. 26, 2016.
(Continued)

*Primary Examiner* — Neil N Turk
(74) *Attorney, Agent, or Firm* — Grogan, Tuccillo & Vanderleeden, LLP

(57) ABSTRACT

Methods, apparatus, systems and articles of manufacture are disclosed herein to implement flexible bioreactor control systems. An example apparatus disclosed herein includes a processor coupled to a memory, the processor programmed to determine whether the map value included in the process task object is a valid map value, the process task object to correspond to a task executed by a bioreactor, a control device or a measurement device of the bioreactor control system configuration, in response to determining the map value is a valid map value, decode the map value to identify the source location of a first input of the process task object, pull a value from the source location to update the input value of the process task object, and facilitate execution of the process task with the input value.

21 Claims, 11 Drawing Sheets

(51) Int. Cl.
      *G05B 19/05*       (2006.01)
      *C12Q 3/00*       (2006.01)
      *G05B 19/042*       (2006.01)

(56) References Cited

U.S. PATENT DOCUMENTS

| | | |
|---|---|---|
| 8,021,871 B2 | 9/2011 | West |
| 8,046,086 B2 | 10/2011 | Pettus et al. |
| 2005/0033453 A1 | 2/2005 | Coogan |
| 2008/0114474 A1 | 5/2008 | Campbell et al. |
| 2010/0099172 A1* | 4/2010 | West ..................... C12M 41/48 |
| | | 435/286.1 |
| 2012/0003728 A1 | 1/2012 | Lanoue et al. |

FOREIGN PATENT DOCUMENTS

| | | |
|---|---|---|
| GB | 2473131 A | 3/2011 |
| JP | 2002269024 A | 9/2002 |
| JP | 2008287719 A | 11/2008 |

OTHER PUBLICATIONS

CN Search Report dated Aug. 15, 2016.
Using Simulink Version 6; Jun. 1, 2004, pp. I-XVI, I, XP00238210, the whole document.
Supplementary European Search Report dated Jun. 10, 2016.
JP Notice of Preliminary Rejection dated Jul. 7, 2017 Based on Application No. 2015-532115.

\* cited by examiner

| PROCESS TASK IDENTIFIER 302 | TRANSFORMER IDENTIFIER 304 | TRANSFORMER STATUS IDENTIFIER 306 | INPUT 1 MAP VALUE 308 | INPUT 1 VALUE 310 | INPUT 2 MAP VALUE 312 | INPUT 2 VALUE 314 | OUTPUT VALUE 316 |
|---|---|---|---|---|---|---|---|
| 0001 | TEMPERATURE RETRIEVER | ACTIVE | 0201 408 | | xxx | xxx | 418 |
| 0002 | MULTIPLIER | ACTIVE | 0001 410 | | 0906 412 | 422 | 420 |
| 0003 | ADDER | ACTIVE | 0002 414 | 424 | 0914 416 | | |
| ⋮ | ⋮ | ⋮ | ⋮ | ⋮ | ⋮ | ⋮ | ⋮ |

PROCESS RECIPE 400

402 ↗ (pointing to row 0001)
404 ↗ (pointing to row 0002)
406 ↗ (pointing to row 0003)

FIG. 4

PROCESS RECIPE 800

| PROCESS TASK IDENTIFIER | TRANSFORMER IDENTIFIER | TRANSFORMER STATUS IDENTIFIER | INPUT 1 MAP VALUE | INPUT 1 VALUE | INPUT 2 MAP VALUE | INPUT 2 VALUE | OUTPUT VALUE |
|---|---|---|---|---|---|---|---|
| 0056 | RETRIEVER | ACTIVE | 0101 812 | | XXX | XXX | 813 |
| 0057 | RETRIEVER | ACTIVE | 0213 814 | | XXX | XXX | 815 |
| 0058 | COMPARATOR | ACTIVE | 0056 816 | | 0057 817 | | 818 |
| 0059 | OUTPUT MODIFIER | ACTIVE | 0058 820 | ... | XXX | XXX | 821 |
| 0060 | BIOREACTOR_01[01] | ACTIVE | 1710 822 | ... | XXX | XXX | 823 |
| | | | ... | | ... | ... | ... |

802 → row 0056
804 → row 0057
806 → row 0058
808 → row 0059
810 → row 0060

FIG. 8

PROCESS RECIPE 900

| PROCESS TASK IDENTIFIER | TRANSFORMER IDENTIFIER | TRANSFORMER STATUS IDENTIFIER | INPUT 1 MAP VALUE | INPUT 1 VALUE | INPUT 2 MAP VALUE | INPUT 2 VALUE | OUTPUT VALUE |
|---|---|---|---|---|---|---|---|
| 0056 | RETRIEVER | ACTIVE | 0101 | | XXX | XXX | |
| 0057 | RETRIEVER | ACTIVE | 0215 912 | | XXX | XXX | 913 |
| 0058 | COMPARATOR | ACTIVE | 0056 | ⋮ | 0057 | XXX | |
| 0059 | OUTPUT MODIFIER | ACTIVE | 0058 | ⋮ | XXX | XXX | |
| 0060 | BIOREACTOR_01[01] | ACTIVE | 1723 914 | ⋮ | XXX | XXX | 915 |
| | | | ⋮ | | ⋮ | ⋮ | ⋮ |

METHODS AND APPARATUS TO IMPLEMENT FLEXIBLE BIOREACTOR CONTROL SYSTEMS

RELATED APPLICATION

This patent arises from a non-provisional application, which claims the benefit of U.S. Provisional Application Ser. No. 61/701,207, which was filed on Sep. 14, 2012, and is hereby incorporated herein by reference in its entirety.

FIELD OF THE DISCLOSURE

This disclosure relates generally to process control systems, and, more particularly, to methods and apparatus to implement flexible bioreactor control systems.

BACKGROUND

Process control systems, like those used in bioreactor control systems, typically include one or more process controllers and input/output (I/O) devices communicatively coupled to at least one host or operator workstation and to one or more process control devices via analog, digital or combined analog/digital buses. The process control devices, which may be, for example, pumps, agitators, mass flow controllers, and transmitters (e.g., temperature, pressure and flow rate sensors), perform functions within the process such as increasing or decreasing fluid flow and measuring process parameters. The process controllers receive signals indicative of process measurements made by the process control devices and/or other information pertaining to the process control devices, use this information to implement a control routine, and then generate control signals that are sent over the buses or other communication lines to the process control devices to control the operation of the process. In this manner, the process controllers may execute and coordinate control strategies using the process control devices via the buses and/or other communication links communicatively coupling the process control devices.

Process control systems are often configured to perform processes in accordance with batch recipes to produce products. Product designers or engineers prepare recipes during a design time and store the recipes to be subsequently used a plurality of times by a process control system. A recipe typically includes a combination of unit procedures, operations, and phases, all of which include instructions to control process equipment (e.g., mixers, pumps, transmitters, valves, etc.) to transfer, mix, etc. ingredients in a process control system to generate a product.

BRIEF SUMMARY

Certain examples provide methods and apparatus to implement flexible bioreactor control systems. An example apparatus to control execution of a process task within a configuration of a bioreactor control system, the process task defined by a process task object that includes a map value to identify a source location for an input value of the process task object includes a processor coupled to a memory. The example processor is programmed to determine whether the map value included in the process task object is a valid map value, the process task object to correspond to a task executed by a bioreactor, a control device or a measurement device of the bioreactor control system configuration, and in response to determining the map value is a valid map value, decode the map value to identify the source location of a first input of the process task object. The example processor is programmed to pull a value from the source location to update the input value of the process task object, and facilitate execution of the process task with the input value.

Another example includes a method to control execution of a process task within a configuration of a bioreactor control system. The example method includes determining whether a map value included in a process task object is a valid map value, the process task object corresponding to a task executed by a process control device within the bioreactor control system, and the map value identifying a source location for an input value of the process task object, and, responsive to determining the map value is a valid map value, pulling a value from the source location to update the input value of the process task object. The example method also includes facilitating execution of the process with the input value.

Another example includes a tangible machine accessible storage medium having instructions thereon that, when executed, cause the machine to at least determine whether a map value included in a process task object is a valid map value, the process task object to correspond to a task executed by a process control device within a bioreactor control system, and the map value to identify a source location for an input value of the process task object. The example instructions to cause the machine to, in response to determining the map value is a valid map value, decode the map value to identify the source location of a first input of the process task object. The example instructions to also cause the machine to pull a value from the source location to update the input value of the process task object, and to facilitate execution of the process task with the input value.

BRIEF DESCRIPTION OF THE DRAWINGS

FIG. 4 illustrates an example process recipe generated by the example process recipe builder of FIG. 2.

FIG. 8 illustrates an example process recipe generated by the example process recipe builder of FIG. 2.

FIG. 9 illustrates an example process recipe generated by the example process recipe builder of FIG. 2.

DETAILED DESCRIPTION

Figure 1A:
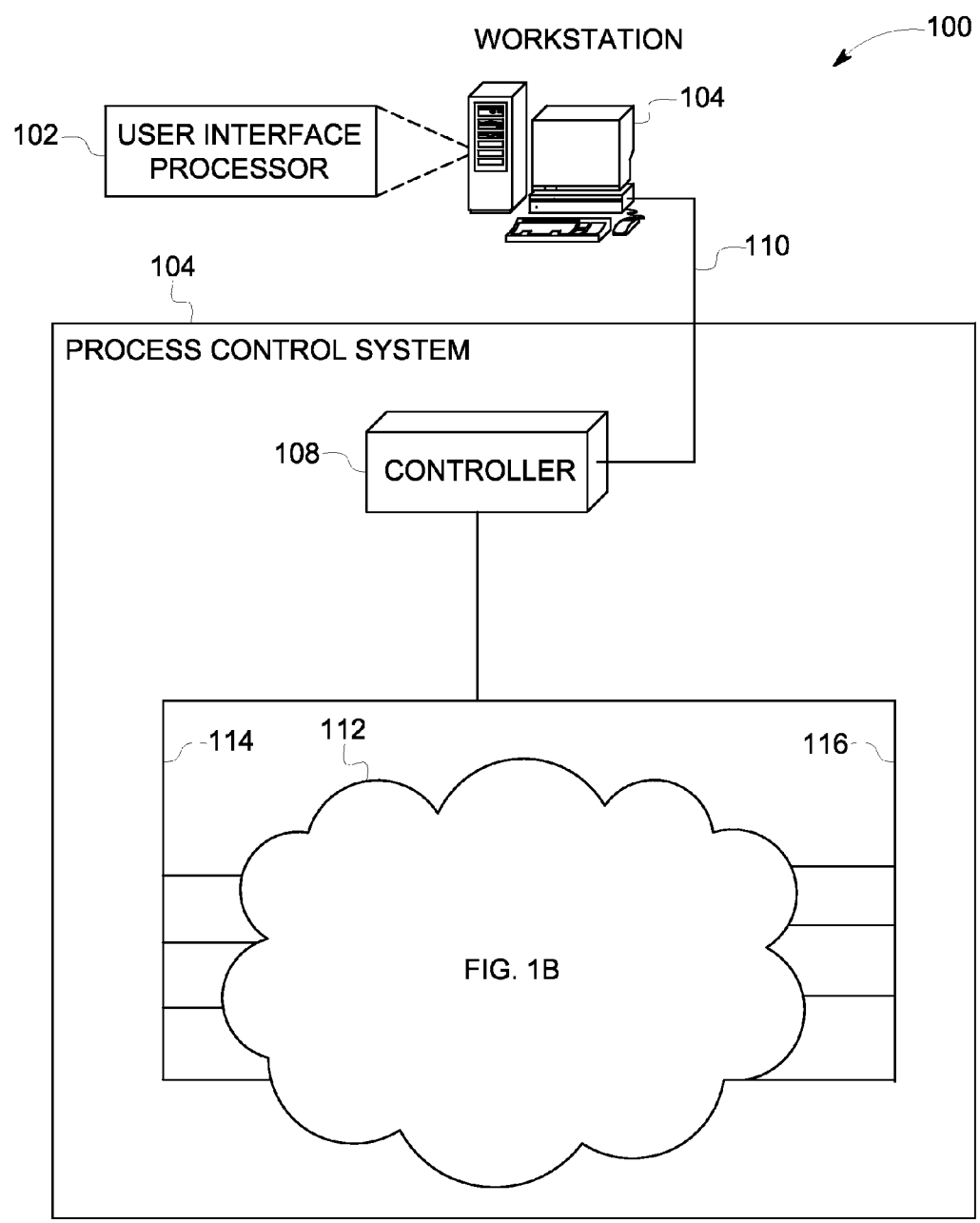
FIG. 1 is a schematic illustration of an example process control environment.

In biotechnology, previous control systems produced products (e.g., pharmaceuticals, etc.) using stainless steel drums. However, using stainless steel drums required costly cleaning and sterilization between batches. For example, each time a new product is produced, the equipment used in the previous product production (sometimes referred to herein as a "batch") had to be properly cleaned and sterilized. In some examples, complex policies and standards must be complied with prior to batch production. For example, prior to producing pharmaceutical products, the control system equipment undergoes an expensive validation process. Thus, in some examples, disposable (sometimes referred to herein as "single-use") process control devices may be used. For example, a bioreactor may be replaced with an irradiated plastic bag. As a result, the cost of maintaining a bioreactor control system may decrease. Furthermore, the use of disposable equipment in a facility (e.g., a plastic bag) enables reduced production downtime due to control system cleaning and sterilizing of the control system equipment.

Regardless of whether the control system uses stainless steel drums or disposable equipment, the equipment still needs to be configured to produce a product. Known control systems may be configured via control system interfacing applications that enable defining equipment (e.g., process control device) configurations and building product recipes with respect to the defined equipment. Known control system interfacing applications include user interfaces (sometimes referred to herein as "control screens") to enable a user (e.g., a product designer, an engineer, etc.) to configure the interaction of the control system equipment. For example, a user may map an input device (e.g., a pH sensor) to an output device (e.g., an acid delivery pump and/or a base delivery pump). In some such examples, the output device may modify its execution based on information received from the input device. For example, if the pH sensor indicates that the pH level of the bioreactor is above a set point, the acid delivery pump may increase acid delivery (e.g., open a valve) to lower the pH level of the bioreactor.

Process recipes (sometimes referred to herein as "batch recipes" or "recipes") define a sequence of equipment actions to produce a product. For example, bioreactor control systems may be used to cultivate bacteria, yeast, microbial fermentations, mammalian cell cultures, etc. In some examples, recipes are built hierarchically and include descriptive information about the product being produced, formula information, equipment requirements and the procedures (e.g., process tasks) used to make the product. In some examples, recipes may be considered templates, which are differentiated by the parameters input. For example, a recipe may include adding a first material into a bag, adding a second material to the bag, mixing the materials in the bag, and transferring the mixture to another device in a control system. Regardless of what the first material and the second material are, the same recipe to transfer a mixture of two materials may be used with the input parameters (e.g., the first material and the second material) changed.

As described above, control system interfacing applications enable a user to configure how control devices interact with each other. To further enable these configurations, some known control system interfacing applications include predefined templates for the control system devices. Control system device templates may be useful when designing a control system as a template may include predefined mappings for a user to quickly define and/or configure. For example, a template for a first sensor may allow a user to map the first sensor (e.g., a dissolved oxygen sensor) to two different types of pumps (e.g., an air pump or an oxygen pump). However, a user who wants to connect the first sensor to a device not included in the template (e.g., a third type of pump such as a glucose feed) would not be possible without custom control system programming. Thus, in some examples, control system interfacing applications may enable a user to re-write source code for the control system device templates. For example, a user may convert a single reactor configuration to a dual reactor configuration. However, this is a cumbersome process that may require multiple weeks of cutting and pasting source code. Furthermore, each time the source code is re-written, the chances of introducing errors in the coding is increased.

Example methods and apparatus disclosed herein enable flexible control system configurations. Unlike prior examples that include predefined device mappings, examples disclosed herein enable a user to map any end device to an input. Examples disclosed herein enable flexible control system configurations by defining primitive (e.g., basic) process tasks of the process control devices. As a result, the different process tasks may be defined as discrete, reusable units of source code. For example, in the two material mixing example described above, a material adding process task may be called twice, once to add the first material, and a second time to add the second material. In some such examples, the source code for mixing remains the same, but the input parameters to the first instance of the material adding process task differs from the second instance of the material adding process task. Furthermore, if the recipe is changed so that three materials are added in a mixture, only the recipe is changed to include a third instance of the material adding process task rather than having to rewrite or modify a two-material mixer block of source code into a three-material mixer block of source code.

Examples disclosed herein define process tasks with corresponding process task objects. An example process task object may include information needed to execute the corresponding process task. For example, an adder process task object may include a first operand (e.g., input) value, a second operand value, a transformation identifying value (e.g., addition) and a results value. Thus, when an instance of the adder process task object is called, the first input and the second input values are sent to an adder, and the resulting value is stored as the adder process task object result value.

However, unlike prior systems, example process task objects disclosed herein also include map values for pulling respective input value(s) to the process task object. Thus, unlike prior systems in which device configurations are limited based on the current mappings included in the control device templates, examples disclosed herein enable flexible bioreactor control system configurations by pulling input values from locations determined by input map values. For example, if a user wants a dissolved oxygen sensor to control the output of a glucose feed pump, examples disclosed herein enable defining the input map value for the glucose feed pump as the output of the dissolved oxygen sensor. Accordingly, before an instance of a glucose feed process task executes, the glucose feed process task object input value is pulled from the dissolved oxygen sensor output value and used as the glucose feed process task object input. Thus, examples disclosed herein enable logically connecting any device output(s) to any other device input(s). Furthermore, examples disclosed herein enable reconfiguring a control system by changing input map values rather than source code. For example, on a first day, the dissolved oxygen sensor may control an oxygen delivery pump (e.g., the oxygen delivery pump pulls the output value of the dissolved oxygen sensor), and on a second day, a pH sensor may control the oxygen delivery pump (e.g., the oxygen delivery pump pulls the output value of the pH sensor).

Figure 1B:
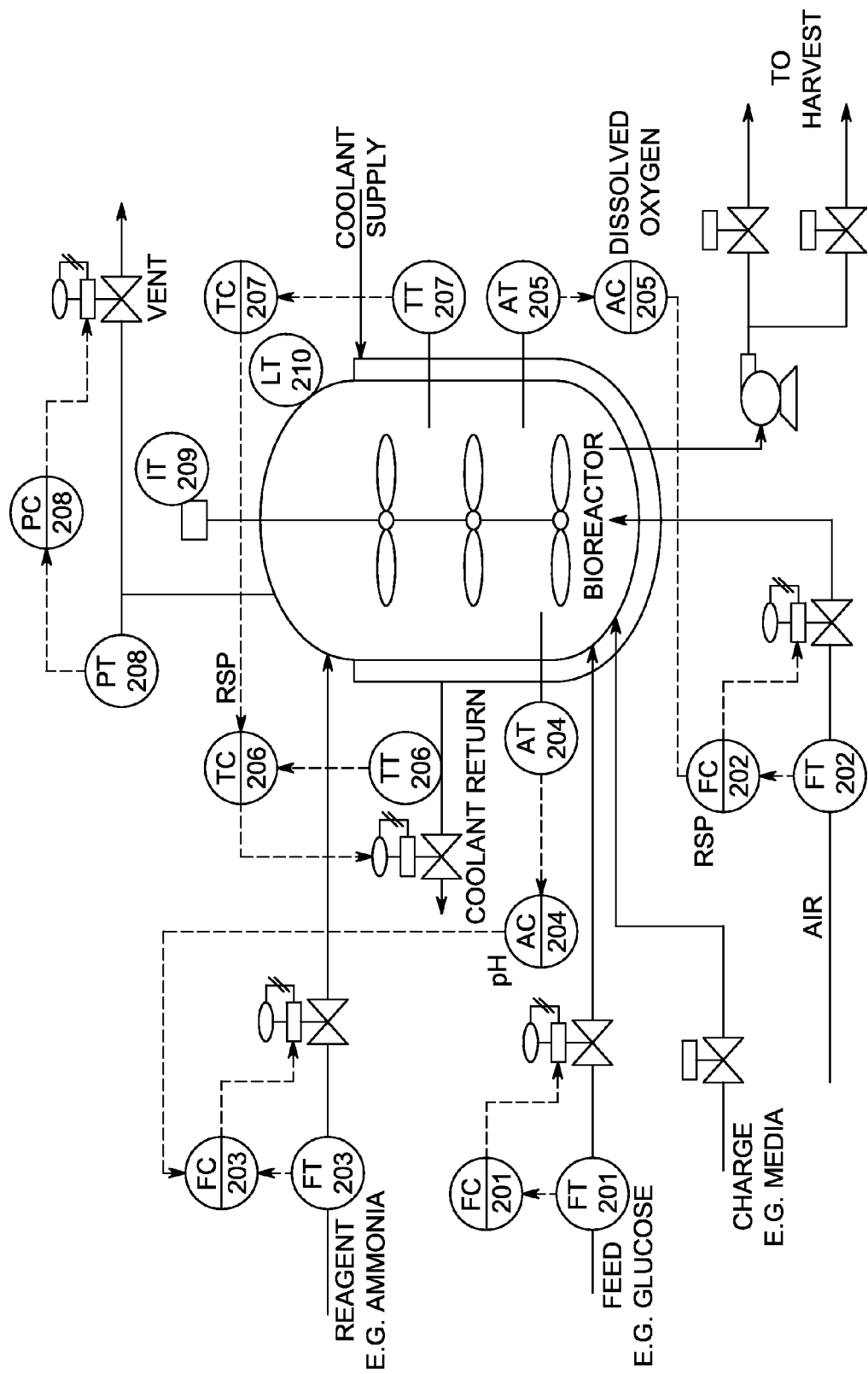

FIG. 1 is a block diagram of an example process control environment 100. The example process control environment 100 includes an example user interface processor 102 and an example bioreactor control system 104 (sometimes referred to herein as a "process control system"). The example user interface processor 102 may be implemented and/or included within an example workstation 106. In other example implementations, the user interface processor 102 may be included within a server, a distributed computing network and/or any other computing device(s) that may be communicatively coupled to the workstation 106.

The example bioreactor control system 104 may include any type of biotechnology or bio-manufacturing facility, structure or system. In some examples, the example process control environment 100 may include other bioreactor control systems (not shown) that may be included within the same facility and/or located at a different facility.

The example process control environment 100 is provided to illustrate one type of system within which the example methods and apparatus described in greater detail below may be advantageously employed. However, the example methods and apparatus described herein may, if desired, be employed in other systems of greater or less complexity than the example process control environment 100 and/or the bioreactor control system 104 shown in FIG. 1.

The example bioreactor control system 104 of FIG. 1 includes an example controller 108 that may be communicatively coupled to the workstation 106 via a network 110. The bioreactor control system 104 also includes process control devices 112 (e.g., input and/or output devices). The process control devices 112 may include any type(s) of process control component(s) capable of receiving inputs, generating outputs, and/or controlling a process or control loop. The process control devices 112 may include control devices such as one or more bioreactors, one or more pumps, one or more mass flow controllers, one or more valves, one or more agitators, etc. Additionally, the process control devices 112 may include one or more measurement or monitoring devices such as pH sensors, temperature sensors, dissolved oxygen sensors, pressure gauges, concentration gauges, flow meters, etc. to measure portions of a process. The control devices may receive instructions from the controller 108 via inputs 114 to execute a specified command and cause a change to the process implemented and/or controlled by the process control devices 112. Furthermore, the measurement or monitoring devices measure process data, environmental data, and/or input device data and transmit the measured data via outputs 116 to the controller 108 as process data. This process data may include the values of variables (or parameters) corresponding to a measured output from each of the process control devices 112.

An example implementation of the bioreactor control system 104 including process control devices 112 may include a bioreactor including a customized jacketed stainless steel vessel, load cells, X-Lift and servo drive for controlling agitation in a plastic bag, exhaust filter heater for ensuring exhaust gas filter does not clog with moisture and cause a bag over pressure interlock and bag hoist, pH/dissolved oxygen sensors/transmitters to control agitation set point or mass flow controller set point or feed pumps, mass flow controllers, metering pumps, bag pressure transmitter(s), resistance temperature detectors (e.g., temperature sensor) and temperature control unit. The described single-use product contact assembly includes all gas filters, agitation system, sparge, probes, ports, pressure sensors sampling, and gas and liquid transfer tubes. In addition, a magnetically coupled, internally-mounted agitator uses no rotation seals or shaft penetrations through disposable assembly. Furthermore, the customized jacketed stainless steel vessel may be used to support and facilitate disposable bag loading and five to one turndown capability function. Temperature control in the example bioreactor control system 104 may be provided by a system temperature controller, which provides rapid heating and cooling. Additionally, the example bioreactor control system 104 includes an option for a heater that uses facility chilled water for cooling (e.g., a Mokon unit).

In the illustrated example of FIG. 1, the example controller 108 may communicate with the process control devices 112 within the bioreactor control system 104 via the inputs 114 and/or the outputs 116. The inputs 114 and the outputs 114 may be implemented by a data bus. In some examples, the data bus may be coupled to intermediate communication components within the bioreactor control system 104. As discussed in detail in connection with FIG. 2, the controller 108 may include a hardware abstractor to receive data from the process control devices 112 and convert (or translate) the data into communications capable of being received and processed by the example controller 108. Additionally, the hardware abstractor may convert (or translate) data or communications from the controller 108 into a data format capable of being processed by the corresponding process control devices 112. In an example, the data bus may be implemented using wired and/or wireless communication protocols such as a process field bus (sometimes referred to as "PROFIBUS") protocol (e.g., PROFIBUS DP), an Ethernet protocol, etc.

The example controller 108 of FIG. 1 manages one or more control routines (e.g., process control loops, algorithms, functions, and/or instructions) to control the process control devices 112 within the bioreactor control system 104. The control routines may include process monitoring applications, alarm management applications, process trending applications, history applications, batch processing management applications, system diagnostic applications, etc. The control routine(s) may ensure that the bioreactor control system 104 produces specified quantities of a desired product within a certain quality threshold. For example, the bioreactor control system 104 may be configured as a batch system that produces a product at a conclusion and/or during a batch process. In other examples, the bioreactor control system 104 may include a continuous process manufacturing system that constantly produces products.

In the illustrated example of FIG. 1, the workstation 106 may be communicatively coupled to the controller 108 via the network 110 (e.g., a local area network (LAN)). The example workstation 106 may include any computing device including a personal computer, a laptop, a server, a controller, etc. Additionally, the workstation 106 may be implemented using any suitable computer system or processing platform (e.g., a processor platform 1000 shown in FIG. 10). For example, the workstation 106 may be implemented using a single processor personal computer, single or multi-processor workstations, etc.

In the illustrated example of FIG. 1, the workstation 106 is shown exterior to the bioreactor control system 104. In other examples, the workstation 106 may be included within the bioreactor control system 104 and/or communicatively coupled directly to the controller 108. Additionally, the process control environment 100 may include routers (not shown) to communicate couple other workstations (not shown) to the controller 108, and/or to communicatively coupled the workstation 106 to other controllers (not shown) within other process controls systems. Further, the process control environment 100 may include a firewall (not shown) to provide remote workstations (e.g., workstations outside of the process control environment 100) access to resources within the process control environment 100.

The example network 110 may be implemented using any desired communication medium and/or protocol. For example, the network 110 may be based on a hardwired or wireless Ethernet communication scheme. However, any other suitable communication medium and/or protocol could be used. Furthermore, although a single network 110 is shown, more than one network and appropriate communication hardware within the workstation 106 may be used to provide redundant communication paths between the workstation 106 and a respective similar workstation (not shown).

The example workstation 106 and/or other workstations with access to the bioreactor control system 104 may be configured to create, view, modify, and/or correct one or more processes within the bioreactor control system 104. The example workstation 106 enables a user to review and/or operate one or more user display screens and/or applications that enable the user to view process control system variables, view process control system states, view process control system conditions, view process control system alarms, view process control system settings (e.g., set points, control variables, process variables, operating states, etc.).

The example workstation 106 includes and/or implements the user interface processor 102 to create, design and/or monitor process control routine(s), and/or process control information transmitted by the controller 108 to identify and/or determine status issues. In the illustrated example, the user interface processor 102 dynamically displays information via a user interface (e.g., a control screen, a graphical user interface (GUI), etc.) to the user. In some examples, the user interface processor 102 displays a mapping display to enable a user to design a process or batch recipe via the bioreactor control system 104. For example, the user may map how the process control devices 112 of the bioreactor control system 104 interact with respect to each other and/or process data provided by the controller 108 and/or other process control devices 112.

In some examples, the user may generate a set point table to configure set points to change automatically according to criteria. As used herein, a set point is a user-entered desired value of a corresponding parameter. For example, a set point for the bioreactor may be set by a user at a pH level of 5.6. As used herein, a process variable is the actual reading of the measurement of the parameter. For example, a measurement or monitoring device 112 (e.g., a pH sensor) may measure the pH level of the bioreactor to be 6.3. As used herein, a control variable is the controller output from the controller 108. In the illustrated example, the pH level of the bioreactor is more basic (e.g., 6.3) than the pH level set point entered by the user (e.g., 5.6). Thus, the controller 108 may transmit an instruction to an acid delivery pump to increase fluid flow (e.g., move a valve towards an open position) to the bioreactor and/or transmit an instruction to a base delivery pump to decrease fluid flow (e.g., move a valve towards a closed position) to the bioreactor.

In the illustrated example, when a user has completed designing a process (e.g., process control device interactions, instructions, procedures, etc.), the user may select a "load," "build," etc. button via a user interface displayed by the user interface processor 102 to build the process. As described in detail in connection with FIG. 2, when the user selects the "load" button, the example user interface processor 102 initiates an example batch manager 204 to manage the components of the example controller 108.

Figure 2:
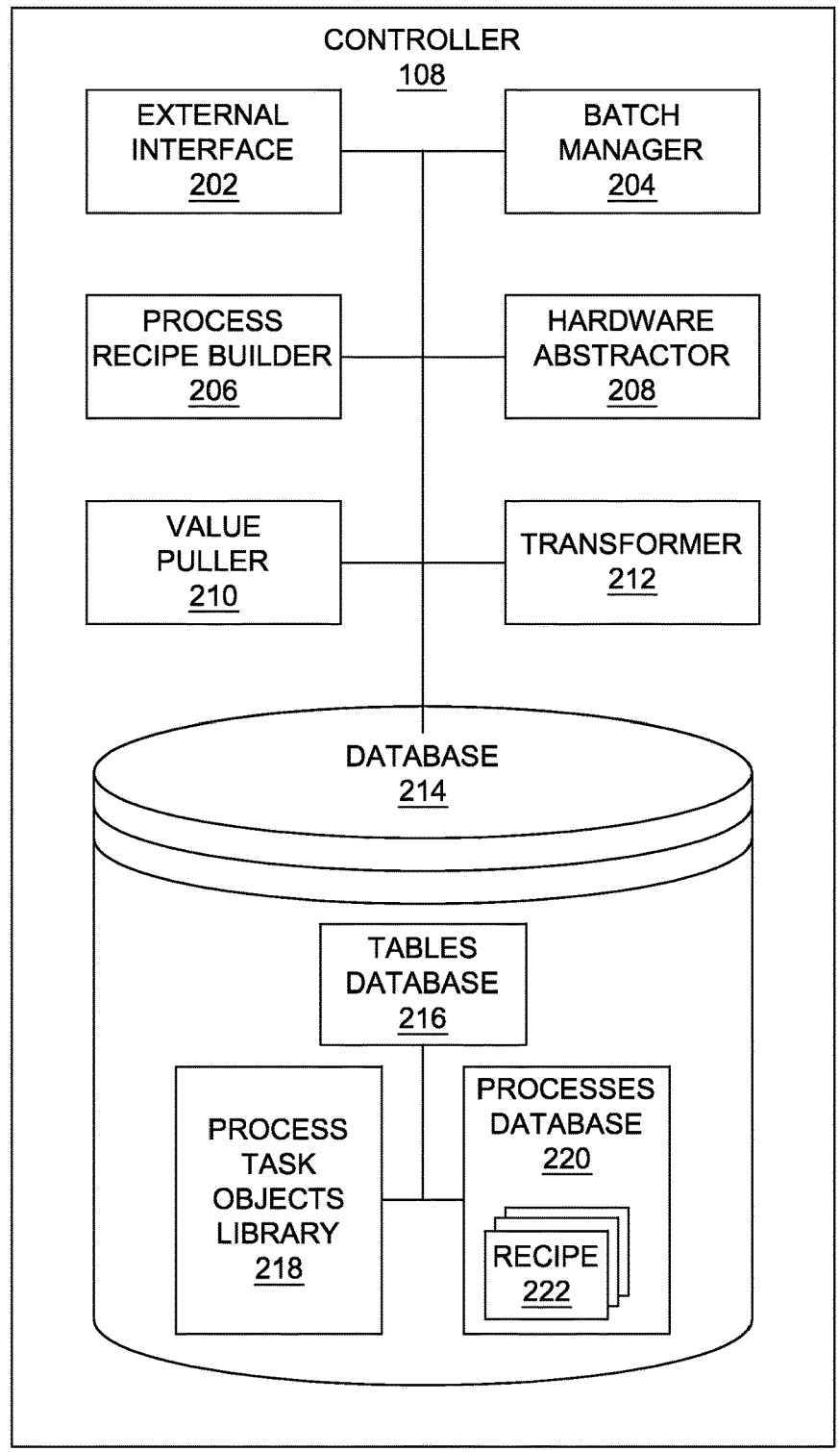
FIG. 2 is a block diagram of an example implementation of the example controller of FIG. 1.

FIG. 2 is a block diagram of an example implementation of the example controller 108 of FIG. 1. In the illustrated example of FIG. 2, the example controller 108 includes an example external interface 202, an example batch manager 204, an example process recipe builder 206, an example hardware abstractor 208, an example value puller 210, an example transformer 212 and an example database 214. The example database 214 includes an example tables database 216, an example process task objects library 218 and an example processes database 220. The example tables database 216 of the illustrated example may store set point tables and/or lookup tables generated by a user via the example user interface processor 102 (FIG. 1) while configuring a process. The example process task objects library 218 of the illustrated example stores templates of process task objects that may be used by the process recipe builder 206 to build (e.g., design, configure, generate, etc.) process recipes. The example processes database 220 stores process recipes (e.g., example process recipe 222) built by the example process recipe builder 206.

In the illustrated example of FIG. 2, the example controller 108 includes the example external interface 202 to enable bi-directional communication between the controller 108 and the example workstation 106 (FIG. 1). The example external interface 202 may be implemented by a wireless communicator to allow the controller 108 to communicate with the example network 110 (FIG. 1) (e.g., a wireless network). However, additionally or alternatively, the external interface 202 may be implemented by any other type of network interface such as, for example, an Ethernet interface, a cellular interface, a Bluetooth® interface, etc.

In the illustrated example of FIG. 2, the example controller 108 includes the example batch manager 204 to manage execution of a batch (or process) recipe. For example, when initiated, the batch manager 204 may orchestrate when the process recipe builder 206, the hardware abstractor 208, the value puller 210 and/or the transformer 212 operate. In some examples, the batch manager 204 is initiated when the user elects to build and/or execute a process. For example, the user may select a "load," "build," etc., button of a user interface. In some examples, the batch manager 204 manages the status of process task objects during execution of a process. For example, the batch manager 204 may determine when a process task object is in an enabled state (e.g., values may be written to the process task object, the transformer 212 may execute a process task object transformation, etc.) or in a disabled state (e.g., values are not written to the process task object). In some such examples, the batch manager 204 may compare process variables (e.g., parameter values measured by example measurement or monitoring devices) to corresponding set points retrieved from a set point table included in the tables database 216. The example batch manager 204 may use the comparison results to determine whether to modify control variables, process task object states, etc.

In the illustrated example of FIG. 2, the example controller 108 includes the example process recipe builder 206 to build process recipes based on a process configured via the user interface processor 102 (FIG. 1). In some examples, the process recipe builder 206 identifies one or more primitive process tasks to execute a portion of the configured process. For example, the process builder 206 may identify a first material adding process task, a second material adding process task, a materials mixing process task and a mixture transferring process task. In the illustrated example, the process builder 206 retrieves a template of a process task object from the process task objects library 218 corresponding to the identified process task(s). A template identifies the elements or fields needed to execute the process task.

Figure 3:
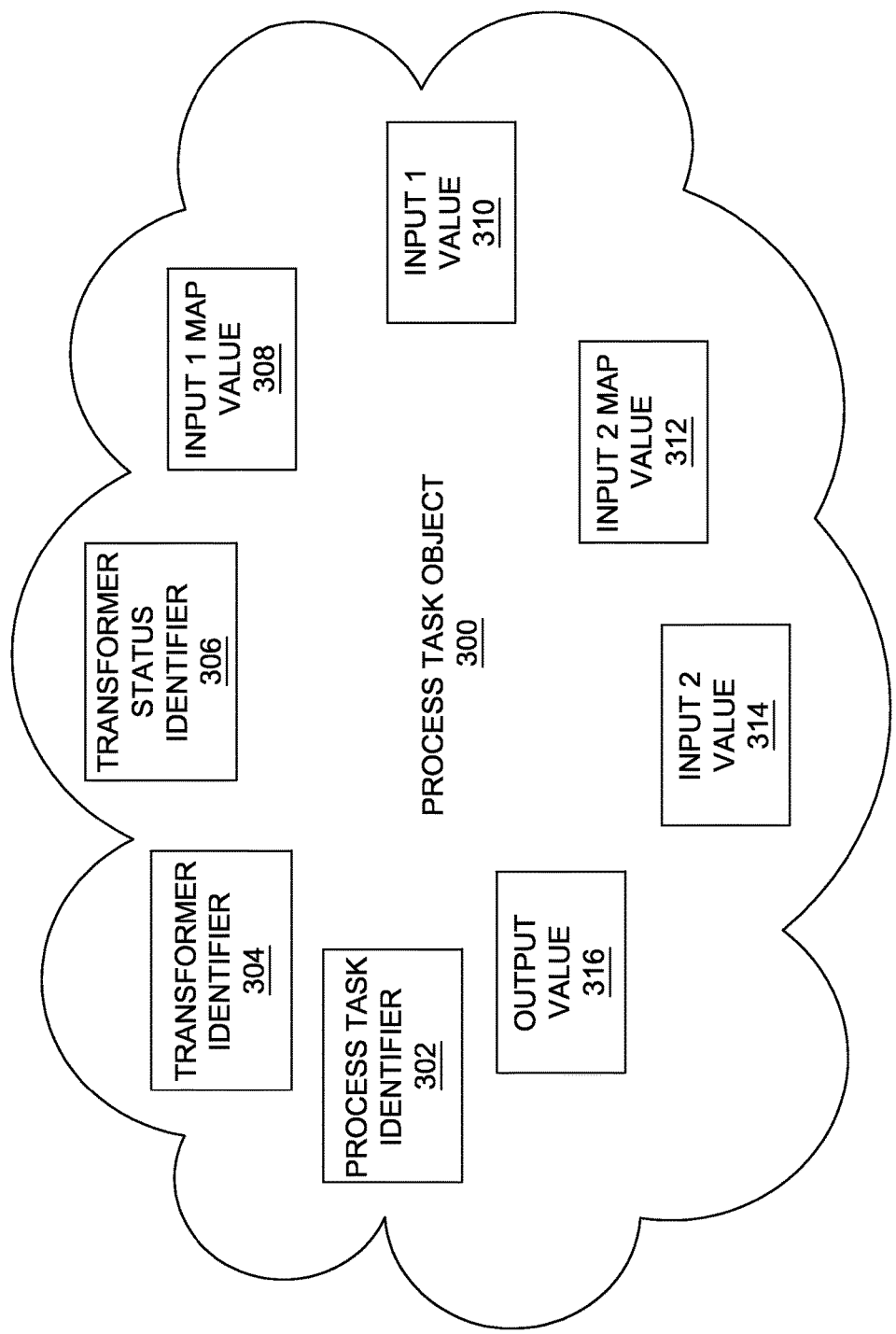
FIG. 3 illustrates an example process task object generated by the example process recipe builder of FIG. 2.

FIG. 3 illustrates an example adder process task object 300 retrieved from the process task objects library 218. In the illustrated example of FIG. 3, the process task object 300 includes an example process task entry identifier 302, an example transformer identifier 304, an example transformer status identifier 306, an example input 1 map value 308, an example input 1 value 310, an example input 2 map value 312, an example input 2 value 314 and an example output value 316. In the illustrated example, the batch manager 204 (FIG. 2) may use the process task entry identifier 302 of a process task object to retrieve the corresponding process task object from the example processes database 220. The example transformer identifier 304 identifies the transformation operation associated with the process task object. For example, an associated transformation operation may include addition, mixing, transferring, etc. In the illustrated example, the transformer status identifier 306 identifies the status of the associated transformation operation. For example, the status may be enabled (e.g., the associated transformation operation identified via the transformer identifier 304 executes) or disabled (e.g., the associated transformation operation identified via the transformer identifier 304 does not execute).

In the illustrated example of FIG. 3, the example input 1 map value 308 identifies the location of the example input 1 map value 310. Similarly, the example input 2 map value 312 identifies the location of the example input 2 map value 314. In the illustrated example, the process recipe builder 206 stores the source location of a process task object input in the corresponding input map value field rather than only the input value in the process task object. As a result, input-output connections are not limited to predetermined (e.g., preconfigured) device mappings. Thus, a process task input may be mapped to retrieve a set point from another process control device or process task, may be mapped to retrieve a set point from the example tables database 216, may be controlled by the example controller 108, or may be mapped to nothing (e.g., may receive an input value from a user via a user interface generated by, for example, the user interface processor 102 (FIG. 1).

In some examples, the example process task objects library 218 may store user-defined process task objects. As used herein, a user-defined process task object is a non-standard (e.g., not pre-configured) process task object. For example, a user may define a user-defined process task object that is specific to their bioreactor control system 104 (FIG. 1). In some such examples, the user may be prompted to define the process task object via a user interface generated by the example user interface processor 102. This may be useful in enabling a user to configure a bioreactor control system unique to their process control environment. In other words, a user is not limited to a finite number of process control system configurations.

Furthermore, by storing the source location for an input value rather than just an input value, the chances of processing an incorrect input value is greatly reduced. That is, the input value is pulled from a specified location (e.g., identified by the corresponding input map value) and, thus, cannot be written into by another output. For example, some prior control systems may enable a user to inadvertently map two output values to the same input value, thereby resulting in an error or the wrong value being processed. As described in detail below in connection with the example value puller 210, rather than an output value being pushed to a process task input, the input map value enables pulling the correct input value from a source location (e.g., another process task output value, a set point table, from the controller 108, etc.), thereby resulting in the correct input value being processed. Thus, an output value may be pulled by one or more input values, but each input value pulls only one output value.

In the illustrated example of FIG. 2, the example process recipe builder 206 populates the one or more process task object fields 302, 304, 306, 308, 310, 312, 314, 316 based on the configured process and stores the process task object with the corresponding process recipe (e.g., the example process recipe 222) in the example processes database 220. FIG. 4 illustrates an example process recipe 400 generated by the process recipe builder 206 including example process task objects 402, 404, 406. In the illustrated example of FIG. 4, the process recipe 400 may be called to convert a temperature from Celsius to Fahrenheit. For example, a temperature sensor may measure the temperature of a bioreactor in Celsius, while an exhaust heater coupled to the bioreactor may operate in Fahrenheit values. Thus, the example process recipe builder 206 may generate the process recipe 400 to convert the measured temperature to Fahrenheit.

For example, to convert temperatures, the process recipe 400 may include a first process task to retrieve the temperature in Celsius from the temperature sensor, a second process task to multiply the retrieved temperature in the first process task by 9/5, and a third process task to add 32 to the product calculated in the second process task. The calculated sum at the completion of the third process task may then be used by, for example, the exhaust heater to determine whether to increase the temperature of the bioreactor. Accordingly, the example process recipe builder 206 populates the input map value fields of the respective process task objects. For example, input 1 map value field 408 of the process task object 402 (e.g., the temperature retrieving process task) corresponds to the output of an exhaust filter temperature sensor, input 1 map value 410 and input 2 map value 412 of the process task object 404 (e.g., the multiplying process task) correspond to the output of the first process task object (e.g., output value 418) and a first lookup table entry (e.g., "0906"), respectively, and input 1 map value 414 and input 2 map value 416 of the process task object 404 (e.g., the adding process task) correspond to the output of the second process task object (e.g., output value 420) and a second lookup table entry (e.g., "0914"). As described in detail in connection with the example value puller 210, the value puller 210 decodes each of the map values to identify the corresponding source locations, pulls (e.g., retrieves) the corresponding values from the identified source locations, and stores the pulled values in the corresponding input value fields of the process task objects.

In the illustrated example of FIG. 2, the example controller 108 includes the example hardware abstractor 208 to convert (or translate) data input to the controller 108 by the process control devices 112 (FIG. 1), and to convert (or translate) data output from the controller 108 to the process control devices 112. For example, the hardware abstractor 208 may read (or receive) output values of the process control devices 112 and the data into communications capable of being received and processed by the example batch manager 204. In addition, the hardware abstractor 208 may convert data stored in the examples processes database 220 into communications capable of being received and processed by the corresponding process control devices 112. In some examples, the hardware abstractor 208 may translate analog data into digital values and/or translate digital values into analog data.

In some examples, the example hardware abstractor 208 is initiated by the example batch manager 204 during execution of a process recipe. In some such examples, the hardware abstractor 208 continuously (or substantially near continuously) (e.g., five times per second) scans the process control devices 112 and/or the processes database 220 for changes in values. For example, when an output value field of a process task object is updated, the hardware abstractor 208 may process the updated value and convert the value into data capable of being received and processed by the corresponding process control device 112. In some examples, the hardware abstractor 208 may update values for process task objects that are in an active state as determined by the transformer status identifiers 306 (FIG. 3) of the corresponding process task objects. In some such examples, the hardware abstractor 208 may skip (or defer) updating values when the transformer status identifiers 306 indicate the corresponding process task object is in an inactive state.

In the illustrated example of FIG. 2, the example controller 108 includes the example value puller 210 to pull input values from source locations and store the input value in the corresponding input value field of the process task objects. In some examples, the value puller 210 iteratively reads through process task objects of a process recipe and pulls the corresponding input values from the source location identified by the corresponding input map value when initiated by the batch manager 204. As described in detail in connection with the example value puller of FIG. 5, the value puller 210 may retrieve a process task object from the example processes database 220, parse the retrieved process task object to find a map value, decode the map value to identify the source location for the corresponding input value, retrieve (e.g., pull) the value from the source location, and update the process task object with the retrieved value.

In the illustrated example of FIG. 2, the example controller 108 includes the example transformer 212 to perform a transformation operation of a called (e.g., executing) process task object. In some examples, the controller 108 may include more than one transformer 212. In some such examples, each of the transformers 212 may perform a specific transformation operation. For example, a first transformer 212 may operate as an adder, a second transformer 212 may operate as a multiplier, etc. In some examples, the controller 108 may include more than one transformer 212, but the transformation operation may vary based on instructions received by the batch manager 204 and/or the example transformer identifier 304 (FIG. 3). For example, during a first cycle, a first transformer 212 may operate as an adder and a second transformer 212 may operate as a multiplier, and during a second cycle, both the first and second transformers 212 may operate as multipliers. In the illustrated example of FIG. 2, the example batch manager 204 stores the result of a transformation operation executed by the transformer 212 in the output value of the corresponding process task object. For example, when the process task object 404 is called (e.g., the transformer 212 is operating as a multiplier), the batch manager 204 stores the product (e.g., the result of the multiplication) in output value 420 of the process task object 404.

While an example manner of implementing the controller 108 of FIG. 1 is illustrated in FIG. 2, one or more of the elements, processes and/or devices illustrated in FIG. 2 may be combined, divided, re-arranged, omitted, eliminated and/or implemented in any other way. Further, the example external interface 202, the example batch manager 204, the example process recipe builder 206, the example hardware abstractor 208, the example value puller 210, the example transformer 212, the example database 214, the example tables database 216, the example process task objects library 218, the example processes database 220 and/or, more generally, the example controller 108 of FIG. 1 may be implemented by hardware, software, firmware and/or any combination of hardware, software and/or firmware. Thus, for example, any of the example external interface 202, the example batch manager 204, the example process recipe builder 206, the example hardware abstractor 208, the example value puller 210, the example transformer 212, the example database 214, the example tables database 216, the example process task objects library 218, the example processes database 220 and/or, more generally, the example controller 108 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example external interface 202, the example batch manager 204, the example process recipe builder 206, the example hardware abstractor 208, the example value puller 210, the example transformer 212, the example database 214, the example tables database 216, the example process task objects library 218 and/or the example processes database 220 is/are hereby expressly defined to include a tangible computer readable storage device or storage disk such as a memory, a digital versatile disk (DVD), a compact disk (CD), a Blu-ray disk, etc. storing the software and/or firmware. Further still, the example controller 108 of FIG. 1 may include one or more elements, processes and/or devices in addition to, or instead of, those illustrated in FIG. 2, and/or may include more than one of any or all of the illustrated elements, processes and devices.

Figure 5:
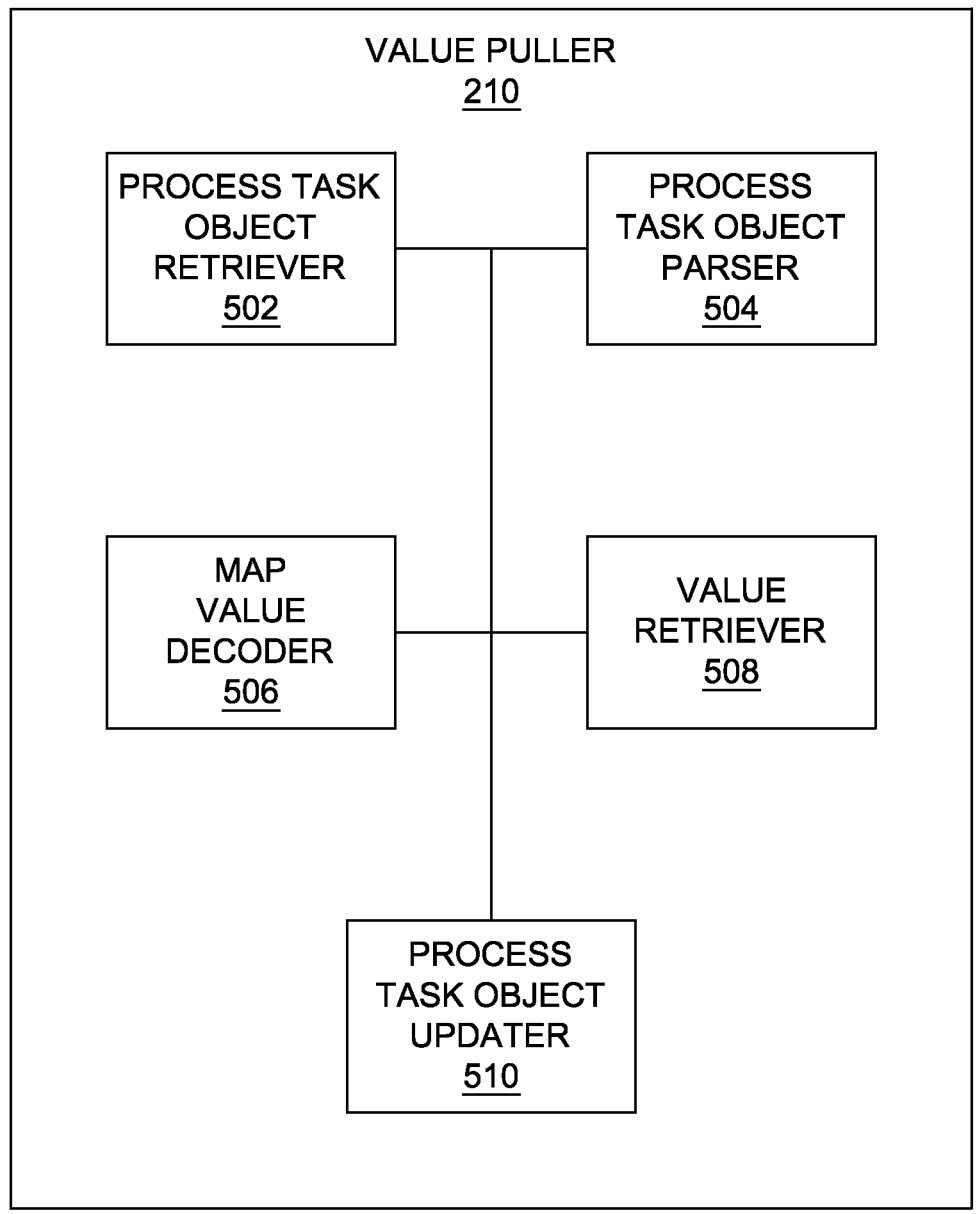
FIG. 5 is a block diagram of an example implementation of the example value puller of FIG. 2.

FIG. 5 is a block diagram of an example implementation of the example value puller 210 of FIG. 2. In the illustrated example of FIG. 5, the example value puller 210 includes an example process task object retriever 502, an example process task object parser 504, an example map value decoder 506, an example value retriever 508 and an example process task object updater 510.

In the illustrated example of FIG. 5, the example value puller 210 includes the example process task object retriever 502 to retrieve process task object(s) from the example processes database 220 (FIG. 2) to pull input values included in the respective process task object. In some examples, the process task object retriever 502 iteratively retrieves the process task objects. For example, the process task object retriever 502 may delay retrieving the example process task object 404 (FIG. 4) of the example process recipe 400 (FIG. 4) until the value puller 210 completes processing of example process task object 402 (FIG. 4). In some examples, the process task object retriever 502 may retrieve more than one process task object from the processes database 220 and store them in a temporary storage such as a buffer or cache. In some such examples, the process task object retriever 502 retrieve the process task objects from the temporary storage one-at-a-time for further processing. In some examples, the process task object retriever 502 may retrieve a map value included in a process task object rather than the process task object. In some such examples, the process task object retriever 502 may communicate the map value to the example map value decoder 506 to decode.

In the illustrated example of FIG. 5, the example value puller 210 includes the example process task object parser 504 to parse fields of a retrieved process task object to identify a map value included in the process task object. For example, while parsing the fields of the example process task object 402, the example process task object parser 504 may identify the input 1 map value 408 (FIG. 4) (e.g., 0201). In some examples, the process task object parser 504 may determine whether the identified map value is a valid map value. For example, a map value ending in two zeros may be indicative of an invalid map value. In some such examples, the example process task object parser 504 may parse the retrieved process task object for another map value and/or notify the example process task object retriever 502 to retrieve another process task object from the example processes database 220.

In the illustrated example of FIG. 5, the example value puller 210 includes the example map value decoder 506 to decode an identified map value to determine the source location for an input value. In the illustrated example of FIG. 5, the map value decoder 506 may map the input value source location to an output of another process task object and/or process control device, to an entry in a table (e.g., a set point table, a lookup table, etc.) included in the example tables database 216, to an output of the batch manager 204, or to nothing. In some examples when the map value maps to nothing (e.g., a null value, an invalid map value, etc.), the value for the corresponding input value may be provided (e.g., input, entered, etc.) by a user.

In the illustrated example of FIG. 5, map values are four digit strings and the first two digits of the map value identify a source type. For example, the first two digits of a map value may identify a device type such as a temperature sensor (e.g., the first two digits (02) of the example process task object 402 input 1 map value 408), a process task (e.g., the first two digits (00) of the example process task object 404 input 1 map value 410), a lookup table (e.g., the first two digits (09) of the example process task object 406 input 2 map value 416), etc.

In the illustrated example of FIG. 5, the second two digits of the map value identify a source number. In some examples, a bioreactor control system may include more than one of a device type. For example, the bioreactor control system 104 (FIG. 1) may include three pumps, four temperature sensors, etc. In some such examples, the second two digits of a map value may identify a certain temperature sensor (e.g., the second two digits (01) of the example process task object 402 input 1 map value 408 identify a first temperature sensor), a process task object (e.g., the second two digits (01) of the example process object 404 input 1 map value 410 identify a first process task object (e.g., the example process task object 402)), a lookup table entry (e.g., the second two digits (14) of the example process object 406 input 2 map value 416 identify the fourteenth entry in a lookup table), etc. Thus, in some examples when the second two digits of a map value are both zero, the map value is an invalid map value.

In the illustrated example of FIG. 5, the example value retriever 508 uses the decoded map value from the example map value decoder 506 to retrieve the corresponding input value from the source location. For example, the map value decoder 506 may identify the source location for the input 2 value 422 of the process task object 404 is the sixth entry (e.g., 06) in a lookup table (e.g., 09). Thus, the example value retriever 508 retrieves the value (e.g., 1.8) from the sixth entry of the lookup table. In the illustrated example of FIG. 5, the example value puller 210 includes the example process task object updater 510 to store the retrieved value in the corresponding input field. For example, the process task object updater 510 may store the retrieved value in the input 2 value 422 field of the process task object 404. In some examples, the process task object updater may also update the example processes database 220 after storing the pulled value in the corresponding input value field.

While an example manner of implementing the value puller 210 of FIG. 2 is illustrated in FIG. 5, one or more of the elements, processes and/or devices illustrated in FIG. 5 may be combined, divided, re-arranged, omitted, eliminated and/or implemented in any other way. Further, the example process task object retriever 502, the example process task object parser 504, the example map value decoder 506, the example value retriever 508, the example process task object updater 510 and/or, more generally, the example value puller 210 of FIG. 2 may be implemented by hardware, software, firmware and/or any combination of hardware, software and/or firmware. Thus, for example, any of the example process task object retriever 502, the example process task object parser 504, the example map value decoder 506, the example value retriever 508, the example process task object updater 510 and/or, more generally, the example value puller 210 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example process task object retriever 502, the example process task object parser 504, the example map value decoder 506, the example value retriever 508, and/or the example process task object updater 510 is/are hereby expressly defined to include a tangible computer readable storage device or storage disk such as a memory, a digital versatile disk (DVD), a compact disk (CD), a Blu-ray disk, etc. storing the software and/or firmware. Further still, the example value puller 210 of FIG. 2 may include one or more elements, processes and/or devices in addition to, or instead of, those illustrated in FIG. 5, and/or may include more than one of any or all of the illustrated elements, processes and devices.

Figure 6:
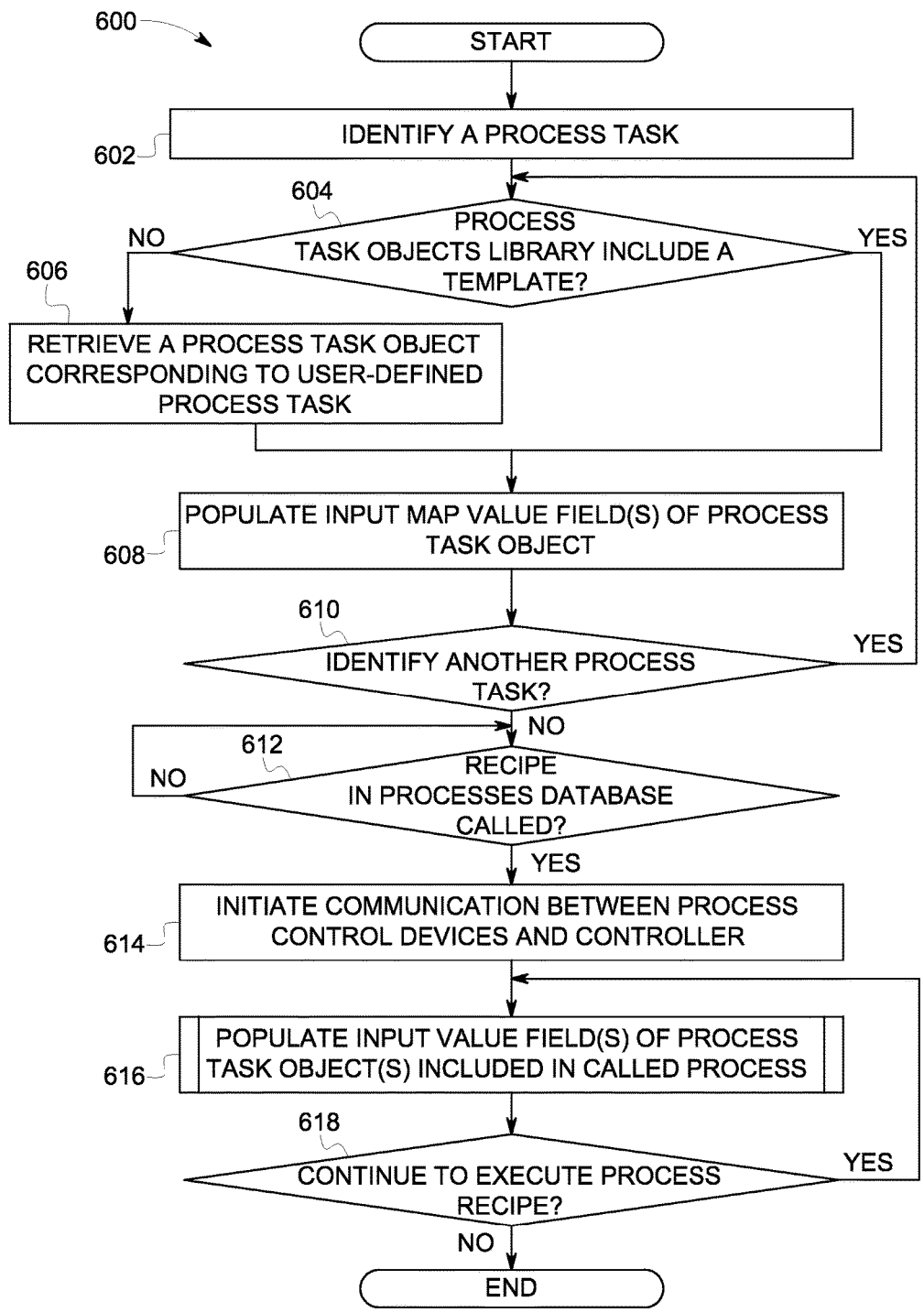
FIG. 6 is a flowchart representative of example machine readable instructions that may be executed to control a bioreactor control system.
Figure 7:
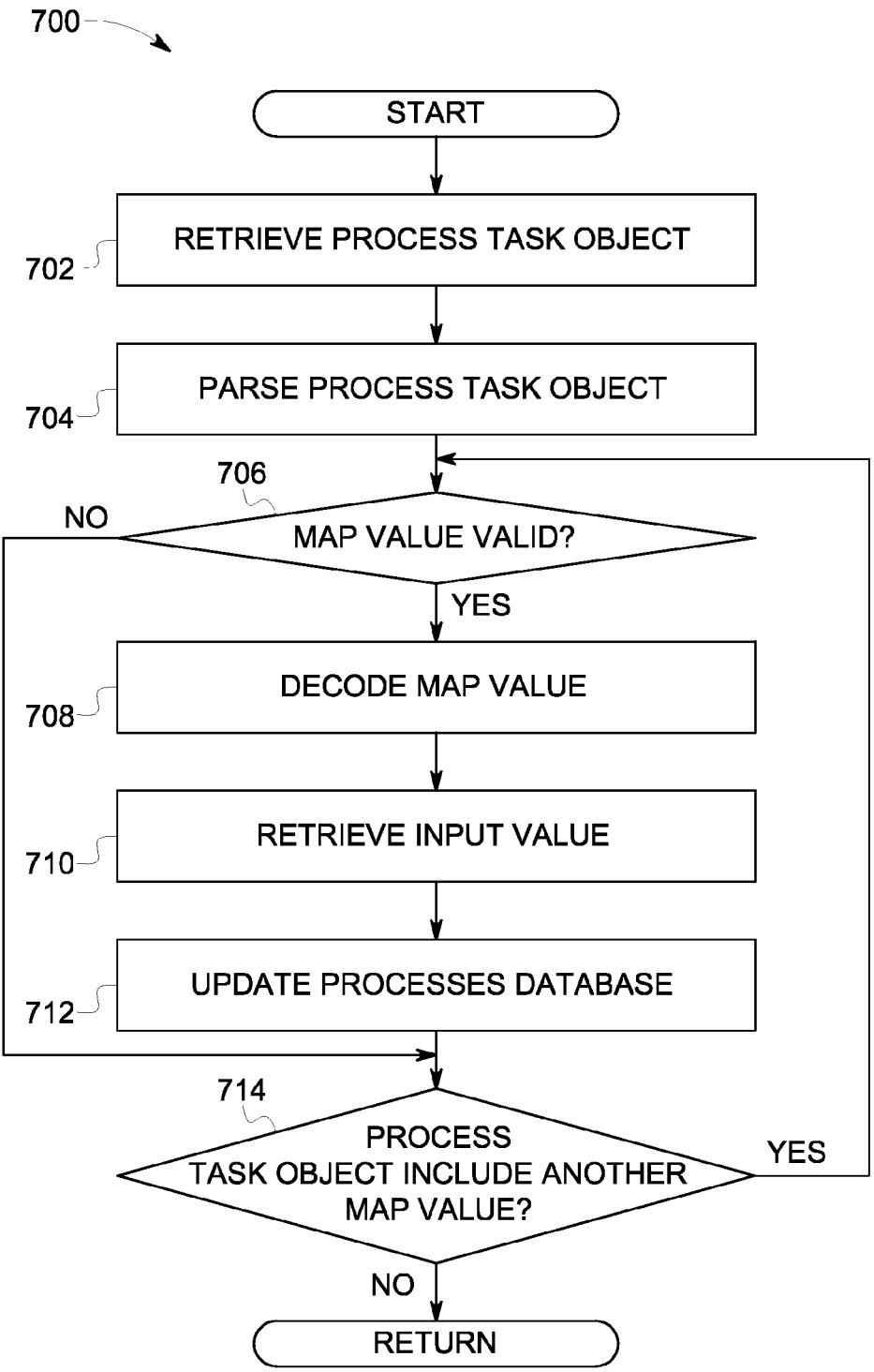
FIG. 7 is a flowchart representative of example machine readable instructions that may be executed to pull input values for a process task object.

A flowchart representative of example machine readable instructions for implementing the controller 108 of FIGS. 1 and/or 2 is shown in FIG. 6. A flowchart representative of example machine readable instructions for implementing the value puller 210 of FIG. 3 is shown in FIG. 7. In these examples, the machine readable instructions comprise a program for execution by a processor such as the processor 1012 shown in the example processor platform 1000 discussed below in connection with FIG. 10. The program may be embodied in software stored on a tangible computer readable storage medium such as a CD-ROM, a floppy disk, a hard drive, a digital versatile disk (DVD), a Blu-ray disk, or a memory associated with the processor 1012, but the entire program and/or parts thereof could alternatively be executed by a device other than the processor 1012 and/or embodied in firmware or dedicated hardware. Further, although the example programs are described with reference to the flowcharts illustrated in FIGS. 6 and/or 7, many other methods of implementing the example controller 108 and/or the value puller 210 may alternatively be used. For example, the order of execution of the blocks may be changed, and/or some of the blocks described may be changed, eliminated, or combined.

As mentioned above, the example processes of FIGS. 6 and/or 7 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 6 and/or 7 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

The program of FIG. 6 begins at block 602 when the example process recipe builder 206 (FIG. 2) identifies a process task in a configured process. For example, while building a process recipe corresponding to a configured process, the process recipe builder 206 may identify a primitive process task (e.g., a multiplying process task, an adding process task, etc.). At block 604, the example process recipe builder 206 determines whether the example process task objects library 218 (FIG. 2) includes a template corresponding to the identified process task. For example, the identified process task may be a preconfigured process task or a user-defined process task defined for use in a specific bioreactor control system. When the example process recipe builder 206 determines the process task objects library 218 does not include a template for the identified process task (block 604) (e.g., the process task is a user-defined process task), control proceeds to block 606 to retrieve a process task object corresponding to the user-defined process task. For example, a user may be prompted to define a process task object for the user-defined process task via a user interface displayed on the example workstation 106 (FIG. 1) via the example user interface processor 102 (FIG. 1).

Otherwise, if, at block 604, the example process recipe builder 206 determines the process task objects library 218 includes a template for the process task, or after a user-defined process task object is retrieved at block 606, then, at block 608, the example process recipe builder 206 populates input map values of the process task object(s) based on the configured process. For example, the process recipe builder 206 may determine that a first process task object uses the output of a second process task object. Thus, the process recipe builder 206 may store a source location (e.g., map value) indicative of the output of the second process task object in a corresponding input map value field of the first process task object.

At block 610, the example process recipe builder 206 determines whether the configured process includes another process task. When the example process recipe builder 206 determines the configured process includes another process task, control returns to block 604 to determine whether the example process task objects library 218 includes a template corresponding to the identified process task. Otherwise, control proceeds to block 612 and the example batch manager 204 (FIG. 2) determines whether a process recipe in the example processes database 220 (FIG. 2) is called. When the batch manager 204 determines a process recipe in the processes database 220 is called at block 612, then, at block 614, the batch manager 204 initiates communication between process control devices 112 (FIG. 1) and the example controller 108 (FIG. 1) of the example bioreactor control system 104. For example, the batch manager 204 may initiate the example hardware abstractor 208 (FIG. 2). As a result, the hardware abstractor 208 may begin translating output values of the process control devices 112 into communications capable of being received and processed by the controller 108, and begin converting output values of the process task objects into communications capable of being received and processed by the process control devices 112.

At block 616, the example value puller 210 (FIG. 2) pulls input values using corresponding map values to populate the input value field(s) of the process task objects included in the called process recipe (e.g., the example recipe 222 (FIG. 2) and/or the example recipe 400 (FIG. 4)). Example processes disclosed herein that may be used to implement block 616 are described below in connection FIG. 7. At block 618, the example batch manager 204 determines whether to continue executing the called process. If the batch manager 204 determines to continue executing the called process, control returns to block 616 to continue populating the input value field(s) of the process task object(s). Otherwise, if, at block 618, the batch manager 204 determines not to continue executing the called process (e.g., due to a process control shutdown event, a bioreactor shutdown event, etc.), the example process of FIG. 6 ends.

The program of FIG. 7 illustrates an example method of populating input values of process task objects included in a called process recipe (e.g., the example recipe 222 (FIG. 2) and/or the example recipe 400 (FIG. 4)). The example program of FIG. 7 may be used to implement block 616 of FIG. 6. The program of FIG. 7 begins at block 702 when the example value puller 210 (FIG. 2) retrieves a process task object from the example processes database 220 (FIG. 2). For example, the example process task object retriever 502 (FIG. 5) may retrieve the example process task object 402 of the example process recipe 400 (FIG. 4). At block 704, the example value puller 210 parses the fields of the retrieved process task object to identify a map value. For example, the example process task object parser 504 (FIG. 5) may identify the input 2 map value 412 (e.g., 0906) in the process task object 404.

At block 706, the example value puller 210 determines whether an identified map value is a valid map value. For example, the map value may correspond to a null value or a zero number device. If the example process task object parser 504 determines the identified map value is not valid, then control proceeds to block 714 to determine if the retrieved process task object includes another map value.

Otherwise, if, at block 706, the example process task object parser 504 determines the map value is a valid map value, then, at block 708, the example value puller 210 decodes the identified map value to identify the source location of the input value corresponding to the identified map value. For example, the example map value decoder 506 (FIG. 5) may use the first two digits of the input 2 map value 412 (e.g., 09) to identify the source type (e.g., a lookup table). The example map value decoder 506 may then use the second two digits of the input 2 map value 412 (e.g., 06) to identify the source number (e.g., the sixth entry). Thus, the example map value decoder 506 identifies the sixth entry in a lookup table as the source location of the input 2 value 422 of the process task object 404. At block 710, the example value puller 210 retrieves the input value from the identified source location. For example, the example value retriever 508 (FIG. 5) may use the decoded map value to retrieve the value (e.g., 1.8) stored in the sixth entry in the lookup table.

At block 712, the example value puller 210 stores the retrieved value in the corresponding input field of the process task object. For example, the process task object updater 510 (FIG. 5) may store the retrieved value (e.g., 1.8) in the input 2 value field 422 of the process task object 404. In some examples, the process task object updater 510 may also update the example processes database 220 with the updated process task object. After the example process task object updater 510 stores the retrieved value at block 712, or if the identified map value is not a valid map value at block 706, then, at block 714, the example value puller 210 determines whether the process task object includes another map value. For example, if the process task object parser 504 determines the retrieved process task object includes another map value, then control returns to block 706 to determine whether the map value is valid. Otherwise, control returns to a calling function or process such as the example program of FIG. 6, and the example process of FIG. 7 ends.

Consider an example in which a user defines a configuration of process control devices of a bioreactor control system and builds a recipe with respect to the defined equipment to cultivate bacteria. For example, a user may want to cultivate a first bacteria that requires an acidic environment and a second bacteria that requires a basic environment. FIG. 8 illustrates an example process recipe 800 generated by the example process builder 206 (FIG. 2) including example process task objects 802, 804, 806, 808, 810 to maintain an acidic environment in an example bioreactor_01[01]. FIG. 9 illustrates an example process recipe 900 generated by the example process builder 206 to maintain a basic environment in the example bioreactor_01 [01]. The example process recipes 800, 900 (e.g., pH control loops) of the illustrated examples may be called by the batch manager (FIG. 2) to maintain the pH level of the example bioreactor_01[01]. For example, while executing the process recipe 800, a pH controller (e.g., a pH controller_05 [04]) may regulate the output of an acid delivery pump_17 [10] based on the detected pH level of the bioreactor_01[01]. In the illustrated examples of FIGS. 8 and/or 9, the first two digits after a device name (e.g., 01, 05 or 17) identify the device type (e.g., a bioreactor, a controller, a pump, respectively), and the second two digits within the brackets (e.g., 01, 04, 10 or 23) identify the device number (e.g., a first bioreactor, a fourth controller, a tenth pump, a twenty-third pump, respectively) within a bioreactor control system.

In the illustrated example of FIG. 8, the example process task objects 802, 804 are retrieving process tasks. That is, the transformer in the process task objects 802, 804 (e.g., a retriever) retrieves a value by pulling the output value corresponding to a map value. For example, the process task object 802 pulls the output value (e.g., a pH sample) corresponding to the input 1 map value 812 (e.g., the example bioreactor_01[01]). In some such examples, the example value puller 210 (FIG. 2) pulls the output value of, for example, a pH sensor coupled to the example bioreactor_01[01] and stores the corresponding value of the process task object 802 (e.g., the input 1 value). The process task object 804 of the illustrated example pulls the output value (e.g., a pH level set point) corresponding to the input 1 map value 814 (e.g., a set point table_09[13]). In some such examples, the example value puller 210 pulls the output value of, for example, the 13th entry in the set point table_09[13] and stores the corresponding value of the process task object 804 (e.g., the input 1 value). Thus, the example process task objects 802, 804 may use the same transformer (e.g., a retriever) to perform their respective operations with only the map value for the respective input 1 values changed. In the illustrated example, the input 1 values of the process task objects 802, 804 are also written as the output values 813, 815, respectively.

In the illustrated example of FIG. 8, the example process task object 806 is a comparing process task. That is, the transformer in the example process task object 806 (e.g., a comparator) compares two values and outputs a value based on the comparison. For example, the pH controller_05[04] may compare the pH sample value from the bioreactor_01 [01] to the pH level set point value in the set point table_09 [13]. In some such examples, during a first iteration, the example value puller 210 pulls the output value of the process task object 802 (e.g., input 1 map value 816), and, during a second iteration, the example value puller 210 pulls the output value of the process task object 804 (e.g., input 1 map value 817). In the illustrated example of FIG. 8, the comparator transformer stores a control value (e.g. output value 818) based on the comparison results.

In some examples, the process task objects 802, 804, 806 may be combined into a single process task object. For example, rather than the input 1 map value 816 mapping to the process task object 802, which retrieved the pH level of the bioreactor_01[01], the input 1 map value of the process task object 806 may map to the bioreactor_01[01]. In addition, the input 2 map value 817 may map to the set point value_09[13], as retrieved in the process task object 804, rather than to the output value of the process task object 804.

In the illustrated example of FIG. 8, the example process task object 808 is an output modifying process task. That is, the transformer in the example process task object 808 (e.g., an output modifier) modifies the fluid flow output by, for example, a pump. For example, the acid delivery pump_17 [10] may vary the amount of acid output in response to a control value from a controller. In some such examples, the example value puller 210 pulls the output value of the process task object 806 (e.g., input 1 map value 820) and modifies the amount of acid output accordingly. In the illustrated example of FIG. 8, the output modifier transformer stores the modified amount of output acid in the output value 821 field of the example process recipe 800.

In the illustrated example of FIG. 8, the example process task object 810 is a fluid flow inputting process task. For example, the bioreactor_01[01] inputs the acid fluid flow from the example acid delivery pump_17[10]. In some such examples, the example value puller 210 pulls the output value of the process task object 808 (e.g., input 1 map value 822) to determine the acid fluid flow input. In the illustrated example of FIG. 8, the example bioreactor_01[01] stores the amount of acid input (e.g., delivered) in the output value field 823 of the example process recipe 800.

Thus, in the illustrated example of FIG. 8, the example process 800 may be used in a bioreactor control system to maintain the pH level of the bioreactor_01[01] at an acidic environment.

FIG. 9 illustrates the example process recipe 900 generated by the example process builder 206 including example process task objects 902, 904, 906, 908, 910. In the illustrated example of FIG. 9, the pH controller_05[04] may regulate the output of a base delivery pump_17[23] based on the detected pH level of the bioreactor_01[01]. Thus, the example process recipe 800 corresponds to a first configuration of a bioreactor control system (e.g., the example bioreactor_01[01] coupled to the pH controller_05[04] and the acid delivery pump_17[10]), while the example process recipe 900 corresponds to a second configuration of a bioreactor control system (e.g., the example bioreactor_01 [01] coupled to the pH controller_05[04] and the base delivery pump_17[23]).

In the illustrated example of FIG. 9, the example process task objects 902, 906, 908 are the same as the corresponding process task objects 802, 806, 808 of FIG. 8. That is, the example process task object 902 retrieves a pH sample value of the example bioreactor_01[01], the example process task object 906 compares the output values of the two previous process task objects (e.g., process task objects 902, 904), and the example process task object 908 modifies the amount of fluid output by a pump.

In the illustrated example of FIG. 9, the example process task object 904 is a retrieving process task object. However, unlike in the example process task object 804 (FIG. 8), the retriever transformer of the example process task object 904 retrieves the pH set point value for a basic environment. That is, the example value puller 210 (FIG. 2) pulls the output value corresponding to the input 1 map value 912 (e.g., the set point table_02[15]) and stores the pulled value in the output value field 913 of the example process recipe 900.

In the illustrated example of FIG. 9, the example process task object 910 is a fluid flow inputting process task. However, unlike in the example process task object 810 (FIG. 8), the bioreactor_01[01] inputs the base fluid flow from the example base delivery pump_17[23]. In some such examples, the example value puller 210 pulls the output value of the process task object 908 (e.g., input 1 map value 914) to determine the base fluid flow input. In the illustrated example of FIG. 9, the example bioreactor_01[01] stores the amount of base input (e.g., delivered) in the output value field 915 of the example process recipe 900.

Thus, the example process recipes 800 and 900 both maintain a desired pH level of the example bioreactor_01 [01]. However, both example process recipes 800 and 900 accomplish this task via different bioreactor control system configurations. As a result, rather than a user re-writing source code to change configurations, examples disclosed herein enable changing bioreactor control system configurations by changing input map values for corresponding process task objects. That is, to change the first configuration of FIG. 8 to the second configuration of FIG. 9, the input map values from where process task objects pull input values are changed. For example, to check whether the pH level of the bioreactor_01[01] is acidic, the example value puller 210 pulls a set point value corresponding to an acidic set point value (e.g., the set point table_09[13] value), and to check whether the pH level of the bioreactor_01[01] is basic, the example value puller 210 pulls a set point value corresponding to a basic set point value (e.g., the set point table_09[23] value). Thus, rather waiting to implement configuration changes in a bioreactor control system, the example value puller 210 enables flexible bioreactor control system configurations by quickly making configuration changes. This may be particularly advantageous when using disposable equipment in a facility. For example, a facility may quickly switch from producing a first product to a second product by replacing the disposable equipment and updating the map values, rather than re-writing source code for the configuration.

Consider an example in which unknown equipment is used in a bioreactor control system. For example, a user may wish to couple an unknown component (e.g., a specific component designed by the user to process information in a certain manner, a brand and/or style component with unknown characteristics, etc.) to a pump in a bioreactor control system. In some such examples, the user may couple the unknown component such as a flow sensor to a spare or auxiliary input of a bioreactor in the bioreactor control system. The user may then create a transformation object (e.g., a lookup table) that allows unit conversion from the units of the unknown component to the expected units of the known component. For example, the transformation object may convert the scale range of the unknown flow sensor to units expected by the pump. In some such examples, a process recipe for the bioreactor control system may include an example first process task object to retrieve values from the flow sensor, an example second process task object to convert the values from the flow sensor into values for the pump, and a third process task object to cause the pump to retrieve the converted values.

In operation, an input 1 map value of the example first process task object may cause the value puller to retrieve the output value of the flow sensor. The example second process task object may include an input 1 map value to cause the value puller to pull the output value of the example first process task object (e.g., the output value of the flow sensor) for use by the transformation object. The example third process task object may include an input 1 map value to cause the value puller to pull the output value of the second process task object (e.g., the converted value via the transformation object) for use by the pump. In this manner, the value puller enables using an unknown component in a bioreactor control system without writing custom software for the bioreactor control system that includes the unknown component.

Figure 10:
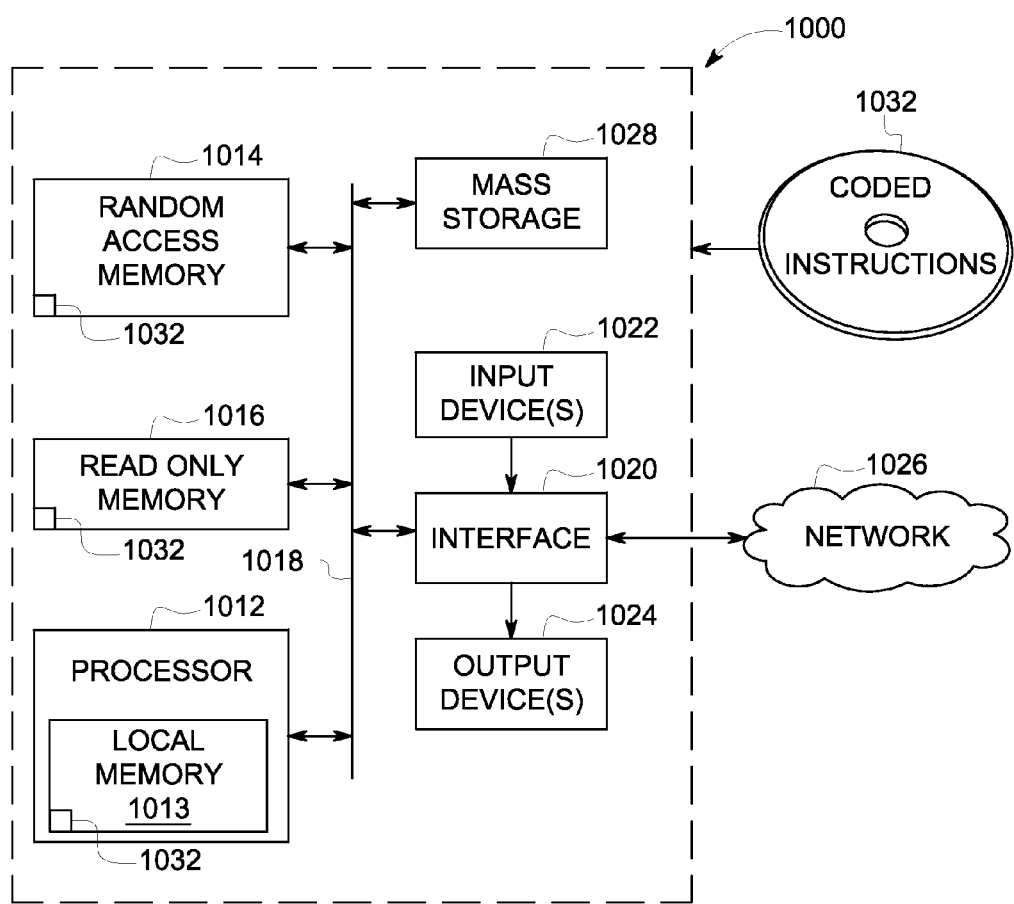
FIG. 10 is a block diagram of an example processing platform capable of executing the example machine readable instructions of FIG. 6 to implement the example controller of FIGS. 1 and/or 2, and/or the example machine readable instructions of FIG. 7 to implement the example value puller of FIGS. 2 and/or 5, respectively.

FIG. 10 is a block diagram of an example processor platform 1000 capable of executing the instructions of FIG. 6 to implement the controller 108 of FIGS. 1 and/or 2, and/or the instructions of FIG. 7 to implement the value puller 210 of FIGS. 2 and/or 5. The processor platform 1000 can be, for example, a server, a personal computer, a mobile device (e.g., a cell phone, a smart phone, a tablet such as an iPad™), a personal digital assistant (PDA), an Internet appliance, or any other type of computing device.

The processor platform 1000 of the illustrated example includes a processor 1012. The processor 1012 of the illustrated example is hardware. For example, the processor 1012 can be implemented by one or more integrated circuits, logic circuits, microprocessors or controllers from any desired family or manufacturer.

The processor 1012 of the illustrated example includes a local memory 1013 (e.g., a cache). The processor 1012 of the illustrated example is in communication with a main memory including a volatile memory 1014 and a non-volatile memory 1016 via a bus 1018. The volatile memory

1014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 may be implemented by flash memory and/or any other desired type of memory device. Access to the main memory 1014, 1016 is controlled by a memory controller.

The processor platform 1000 of the illustrated example also includes an interface circuit 1020. The interface circuit 1020 may be implemented by any type of interface standard, such as an Ethernet interface, a universal serial bus (USB), and/or a PCI express interface.

In the illustrated example, one or more input devices 1022 are connected to the interface circuit 1020. The input device(s) 1022 permit(s) a user to enter data and commands into the processor 1012. The input device(s) can be implemented by, for example, an audio sensor, a microphone, a keyboard, a button, a mouse, a touchscreen, a track-pad, a trackball, isopoint and/or a voice recognition system.

One or more output devices 1024 are also connected to the interface circuit 1020 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1020 of the illustrated example, thus, typically includes a graphics driver card, a graphics driver chip or a graphics driver processor.

The interface circuit 1020 of the illustrated example also includes a communication device such as a transmitter, a receiver, a transceiver, a modem and/or network interface card to facilitate exchange of data with external machines (e.g., computing devices of any kind) via a network 1026 (e.g., an Ethernet connection, a digital subscriber line (DSL), a telephone line, coaxial cable, a cellular telephone system, etc.).

The processor platform 1000 of the illustrated example also includes one or more mass storage devices 1028 for storing software and/or data. Examples of such mass storage devices 1028 include floppy disk drives, hard drive disks, compact disk drives, Blu-ray disk drives, RAID systems, and digital versatile disk (DVD) drives.

The coded instructions 1032 of FIGS. 6 and/or 7 may be stored in the mass storage device 1028, in the volatile memory 1014, in the non-volatile memory 1016, and/or on a removable tangible computer readable storage medium such as a CD or DVD.

From the foregoing, it will appreciate that the above disclosed methods, apparatus and articles of manufacture enable increased flexibility in logically connecting any device output(s) to any other device input(s). Furthermore, examples disclosed herein enable improved reconfiguring a control system by changing input map values rather than source code.

It is noted that this patent claims priority from U.S. Provisional Application Ser. No. 61/701,207, which was filed on Sep. 14, 2012, and is hereby incorporated by reference in its entirety.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus for configuring a bioreactor control system comprising:
a memory device that stores a process task object that defines a process task to be executed by a first process control device of the bioreactor control system, the first process control device having an input mapped to an output of a second process control device of the bioreactor control system, the process task object including a map value that identifies a source location for an input value of the process task object, the input value defined by a third process control device of the bioreactor control system;
a hardware abstractor in electronic communication with a data bus disposed in the bioreactor control system that connects the hardware abstractor to the first, the second, and the third process control devices; and
a processor coupled to the memory device and the hardware abstractor and configured to:
determine whether the map value is a valid map value;
decode the map value to identify the source location;
pull a value from the source location via the hardware abstractor to update the input value; and
configure the process task to be executed with the input value via the first process control device and the hardware abstractor such that the input of the first process control device is mapped to an output of the third process control device; and
wherein the process task defines an action for producing a product,
the first process control device preforms the action defined by the process task, and
the first, the second, and the third process control devices are each one of a bioreactor, a pump, a flow control device, a valve, an agitator, a ph sensor, a temperature sensor, a dissolved oxygen sensor, a pressure gauge, a concentration gauge, and a flow meter.

2. An apparatus as defined in claim 1, wherein the map value identifies an output of a second process task object.

3. An apparatus as defined in claim 1, wherein the map value identifies a table entry.

4. An apparatus as defined in claim 1, wherein the process task object is one of a plurality of process task objects included in a process recipe.

5. An apparatus as defined in claim 4, wherein the process recipe defines a sequence of actions within the bioreactor control system configuration to produce the product.

6. An apparatus as defined in claim 1, wherein decoding the map value further comprises determining, via the processor, a device type and a device number.

7. An apparatus as defined in claim 1, wherein the process task transforms the input value into an output value when executed.

8. A method for configuring a bioreactor control system comprising:
determining, via a processor of an apparatus for configuring the bioreactor control system, whether a map value included in a process task object stored in a memory device of the apparatus for configuring the bioreactor control system is a valid map value, the process task object corresponding to a task executed by a first process control device of the bioreactor control system, the first process control device having an input mapped to an output of a second process control device of the bioreactor control system, and the map value identifying a source location for an input value of the process task object, the input value defined by a third process control device of the bioreactor control system;

responsive to determining the map value is a valid map value, pulling, via a hardware abstractor in electronic communication with a data bus disposed in the bioreactor control system and connected to the first, the second, and the third process control devices and operative to facilitate electronic communication between the processor and the first, the second, and the third process control devices, a value from the source location to update the input value of the process task object; and configuring, via the processor and the hardware abstractor, the process task to be executed with the input value via the first process control device such that the input of the first process control device is mapped to an output of the third process control device; and wherein the process task defines an action for producing a product, the first process control device preforms the action defined by the process task, and the first, the second, and the third process control devices are each one of a bioreactor, a pump, a flow control device, a valve, an agitator, a ph sensor, a temperature sensor, a dissolved oxygen sensor, a pressure gauge, a concentration gauge, and a flow meter.

9. A method as defined in claim 8, wherein the map value identifies an output of a second process task object.

10. A method as defined in claim 8, wherein the map value identifies a table entry.

11. A method as defined in claim 8, wherein the process task object is one of a plurality of process task objects included in a process recipe.

12. A method as defined in claim 11, wherein the process recipe defines a sequence of actions within the bioreactor control system configuration to produce the product.

13. A method as defined in claim 8, wherein decoding the map value further comprises determining a device type and a device number of a process control device in the bioreactor control system.

14. A method as defined in claim 8, wherein configuring, via the processor, the process task to be executed with the input value via the first process control device further comprises transforming the input value into an output value.

15. A non-transitory computer readable medium having instructions that, when executed, cause a processor of an apparatus for configuring a bioreactor control system to at least:

determine whether a map value included in a process task object stored in a memory device of the apparatus for configuring the bioreactor control system is a valid map value, the process task object to correspond to a task executed by a first process control device of a bioreactor control system, the first process control device having an input mapped to an output of a second process control device of the bioreactor system, and the map value to identify a source location for an input value of the process task object, the input value defined by a third process control device of the bioreactor control system;

in response to determining the map value is a valid map value, decode the map value to identify the source location of a first input of the process task object;

pull a value from the source location to update the input value of the process task object via a hardware abstractor in electronic communication with a data bus disposed in the bioreactor control system and connected to the first, the second, and the third process control devices and operative to facilitate electronic communication between the processor and the first, the second, and the third process control devices; and configure the process task, via the hardware abstractor, to be executed with the input value via the first process control device such that the input of the first process control device is mapped to an output of the third process control device; and wherein the process task defines an action for producing a product, the first process control device preforms the action defined by the process task, and the first, the second, and the third process control devices are each one of a bioreactor, a pump, a flow control device, a valve, an agitator, a ph sensor, a temperature sensor, a dissolved oxygen sensor, a pressure gauge, a concentration gauge, and a flow meter.

16. A non-transitory computer readable medium as defined in claim 15, wherein the map value identifies an output of a second process task object.

17. A non-transitory computer readable medium as defined in claim 15, wherein the map value identifies a table entry.

18. A non-transitory computer readable medium as defined in claim 15, wherein the process task object is one of a plurality of process task objects included in a process recipe.

19. A non-transitory computer readable medium as defined in claim 18, wherein the process recipe defines a sequence of actions within the bioreactor control system configuration to produce the product.

20. A non-transitory computer readable medium as defined in claim 15, further comprising instructions that, when executed, cause the processor to determine a device type and a device number.

21. A non-transitory computer readable medium as defined in claim 15, further comprising instructions that, when executed, cause the processor to transform the input value into an output value.

* * * * *